United States Patent [19]

Strand et al.

[11] Patent Number: 5,084,443

[45] Date of Patent: Jan. 28, 1992

[54] PROMOTING EXPRESSION OF ACETYLCHOLINE RECEPTORS WITH LHRH ANTAGONIST

[75] Inventors: Fleur Strand, New York, N.Y.; Jacques-Pierre Moreau, Upton, Mass.

[73] Assignees: Biomeasure, Inc., Hopkinton, Mass.; New York University, New York, N.Y.

[21] Appl. No.: 444,999

[22] Filed: Dec. 4, 1989

[51] Int. Cl.$^5$ .......................... C07K 7/06; C07K 7/20
[52] U.S. Cl. .......................................... 514/15; 514/14
[58] Field of Search .................................. 514/14–15

[56] References Cited

U.S. PATENT DOCUMENTS

| | | | |
|---|---|---|---|
| 4,010,125 | 3/1977 | Schally et al. | 514/15 |
| 4,071,622 | 1/1978 | Johnson et al. | 514/15 |
| 4,075,191 | 2/1978 | Beddell et al. | 514/15 |
| 4,218,439 | 8/1980 | Rivier et al. | 514/15 |
| 4,341,767 | 7/1982 | Nestor et al. | 514/15 |
| 4,395,403 | 7/1983 | Bauer et al. | 514/15 |
| 4,431,635 | 2/1984 | Coy et al. | 514/15 |
| 4,444,759 | 2/1984 | Rivier et al. | 514/15 |
| 4,565,804 | 1/1986 | Rivier et al. | 514/15 |
| 4,569,927 | 2/1986 | Rivier et al. | 514/15 |
| 4,631,270 | 12/1986 | Yankeelov, Jr. et al. | 514/15 |
| 4,632,979 | 12/1986 | Coy et al. | 514/15 |
| 4,642,332 | 2/1987 | Folkers et al. | 514/15 |
| 4,705,778 | 11/1987 | Almquist et al. | 514/15 |

FOREIGN PATENT DOCUMENTS

| | | |
|---|---|---|
| 0049628 | 10/1981 | European Pat. Off. . |
| 0052510 | 11/1981 | European Pat. Off. . |
| 0038135 | 3/1982 | European Pat. Off. . |
| 0081877 | 6/1982 | European Pat. Off. . |
| 0097031 | 6/1983 | European Pat. Off. . |
| 0225746 | 11/1986 | European Pat. Off. . |
| 0277829 | 2/1988 | European Pat. Off. . |
| 2009182 | 11/1978 | United Kingdom . |

OTHER PUBLICATIONS

D. H. Coy et al., LH-Releasing Activity of Potent LH-RH Analogs In Vitro; Biochem. and Biophys. Research Comm.; 67:576-82; (1975).

C. Auclair et al.; Potent Inhibitory Activity of [D-Leu$^6$, Des-Gly-NH$_2$$^{10}$]LHRH Ethylamide on LH/hCO and PRL Testicular Receptor Levels in the Rat; Endo; 101:1890-93; (1977).

D. N. Ishii et al.; Regulation of Nerve Growth Factor Synthesis in Mouse Submaxillary Glands by Testosterone; Jour. of Neuro.; 25:843-51; (1975).

D. Tourwe; The Synthesis of Peptide Analogues with a Modified Peptide Bond; Organic Chemistry.

S. P. Yeagle et al.; Contractile Properties of Rat Fast-Twitch Skeletal Muscle during Reinnervation: Effects of Testosterone and Castration; Exp. Neur.; 82:344-57; (1983).

W. A. Bijlsma et al.; Neurotrophic Factors and Regeneration in the Peripheral Nervous System; Psychoneuroendocrinology; 9:199-215; (1984).

C. Auclair et al.; Inhibition of Testicular Luteinizing Hormone Receptor Level by Treatment with . . . ; Bio. and Biophy. Res. Comm.; 76:855-59; (1977).

D. H. Coy et al.; Peptide Antoagonists of LH-RH: Large Increases in Antiovulatory Activities Produced by Basic D-Amino Acids in the Six Position; Endo.; 110:1445-1447; (1982).

L. P. Weiner; Possible Role of Androgen Receptors in Amyotrophic Lateral Sclerosis; Archives of Neurology; 37:129-31; (Mar. 1980).

G. Vita et al.; Effects of Steroid Hormones on Muscle Reinnervation after Nerve Crush in Rabbit; Experimental Neurology; 80:279-87; (1983).

Primary Examiner—Lester L. Lee
Attorney, Agent, or Firm—Fish & Richardson

[57] ABSTRACT

A method for promoting regrowth of damaged nerve tissue in a mammal, the method comprising administering to the mammal a nerve tissue regrowth promoting amount of an LHRH antagonist namely, N-Acetyl-D-Naphthylalanine-D-para-Cl-Phe-D-Phe-Ser-Tyr-D-Arg-Phe-Arg-Pro-D-Ala-NH$_2$.

2 Claims, 5 Drawing Sheets (List continued on next page.)

OTHER PUBLICATIONS

Folkers et al.; Analogs of the Luteinzing Hormone Releasing Hormone having the Azagly-10 Moiety Moiety with Antiovulatory Activity; Z. Naturforsch. B.; (1984).

Folkers et al.; Antagonists of the Luteinizing Hormone Releasing Hormone with Emphasis on Amino Acids in Position Five; Z. Naturforsch. B.; (1985).

Westor et al.; Pharmacodynamics; J. Med. Chem.; 901170–74; (Jun. 1979).

H. Matsuo et al.; Structure of the Porcine LH and FSH-Releasing Hormone; Biochemical and Biophysical Research Communications; 43:1334–39; (1971).

G. Tolis et al.: Tumor Growth Inhibition in Patients with Prostatic Carcinoma Treated with Luteinizing Hormone-Releasing Hormone Agonists; Proc. Natl. Acad. Sci; 79:1658–1662; (Mar. 1982).

K. Folkers et al.; Antagonists of the Luteinizing Hormone Releasing Hormone (LHRH) with Emphasis on the TRP[7] of the Salmon and Chicken II LHRH's; Biochem. & Biopy.; 123:1221–26; (1984).

K. J. Jones; Steroid Hormones and Neurotrophism: Relationship to Nerve Injury; Metabolic Brain Metabolic Brain Disease; 3:1–18; (1988).

W. A. Yu; Responsiveness of Hypoglossal Neurons to Testosterone in Pre-Pubertal Rats; Braun Research Bulletin; 13:667–72; (1984).

A. V. Schally et al.; Isolation and Properties of the Fish and LH-Releasing Hormone; Biochemical and Biophysical Research Communications; 43:393–99; (1971).

PROMOTING EXPRESSION OF ACETYLCHOLINE RECEPTORS WITH LHRH ANTAGONIST

BACKGROUND OF THE INVENTION

This invention relates to treatment of nerve injury.

Jones (1988, Metabolic Brain Disease 3:1) suggests that steroid hormones "act at the level of RNA and protein synthesis to effect metabolic changes associated with nerve cell survival, elaboration/maintenance of dendritic and axonal processes, synaptogenesis, and neurotransmission", and that both estrogens and androgens have a "stimulatory, growth-like effect on target neurons". Similarly, Yu (1984, Brain Research Bulletin 13:667) demonstrated that "administration of testosterone to adult rats shortened the time course of regeneration of the transected or crushed hypoglossal nerve".

A number of luteinizing hormone releasing hormone (LHRH) analogs have been described which inhibit the release of LHRH, a peptide hormone having the formula pyro-Glu-His-Trp-Ser-Tyr-Gly-Leu-Arg-Pro-Gly-$NH_2$; A. V. Schally et al., Biochem. Biophys. Res. Comm. 43:393 and 1334 (1971). These analogs are called LHRH antagonists. For example, Coy et al. U.S. Pat. No. 4,431,635, hereby incorporated by reference, describes LHRH analogs having the general formula X-$R^1$-$R^2$-$R^3$-Ser-Tyr-$R^4$-Leu-Arg-Pro-$R^5$-$NH_2$, in which X can be Ac; $R^1$ and $R^4$, independently, can be D-Trp or D-p-X-Phe, where X is a halogen or methyl group; $R^2$ can be D-p-X-Phe; $R^3$ can be D-Trp; and $R^5$ can be Gly or D-Ala.

A large number of publications describe LHRH antagonists and their use in various medical applications, e.g., the suppression of gonadal function. For example, Schally and Coy, U.S. Pat. No. 4,010,125, hereby incorporated by reference, describes a decapeptide analog of LHRH of the formula pyro-Glu-His-Trp-Ser-Tyr-D-Trp-Leu-Arg-Pro-Gly-$NH_2$ useful for inducing ovulation and for treating delayed puberty and hypgonadism.

Tolis et al. Proc. Natl. Aca. Sci. 79:1658 (1982), hereby incorporated by reference, suggests that the chronic administration of large doses of two LHRH antagonists ([D-Trp$^6$]LHRH and [D-Ser(But)$^6$-desGly-$NH_2$]LHRH can result in the suppression of pituitary secretion and leydig cell production and the regression of mammary and prostatic endocrine-dependent tumors in animals and humans.

Johnson et al. U.S. Pat. No. 4,071,622, hereby incorporated by reference, describes nonapeptides of the formula pGlu-His-Trp-Ser-Tyr-X-Leu-Arg-Pro-NH-$C_2H_5$, where X is the D form of Tyr, Trp, or Phe, useful for the treatment of mammary tumors.

SUMMARY OF THE INVENTION

The invention features, in one aspect, a method for promoting regrowth of damaged nerve tissue in a mammal, involving administering to the mammal a nerve tissue regrowth promoting amount of an LHRH antagonist.

In another aspect, the invention features a method for inhibiting muscle wasting in a mammal, involving administering to the mammal a muscle preserving amount of an LHRH antagonist.

Regrowth of the damaged nerve tissue according to the invention can result in regeneration of associated muscle tissue, which commonly atrophies following injury to nerve tissue. In addition, muscle tissue can be preserved in cases in which nerve damage is not the direct cause of muscle wasting.

Other features and advantages of the invention will be apparent from the following description of the preferred embodiments thereof, and from the claims.

We first briefly describe the drawings.

DRAWINGS

DESCRIPTION OF THE PREFERRED EMBODIMENTS

Figure 1:
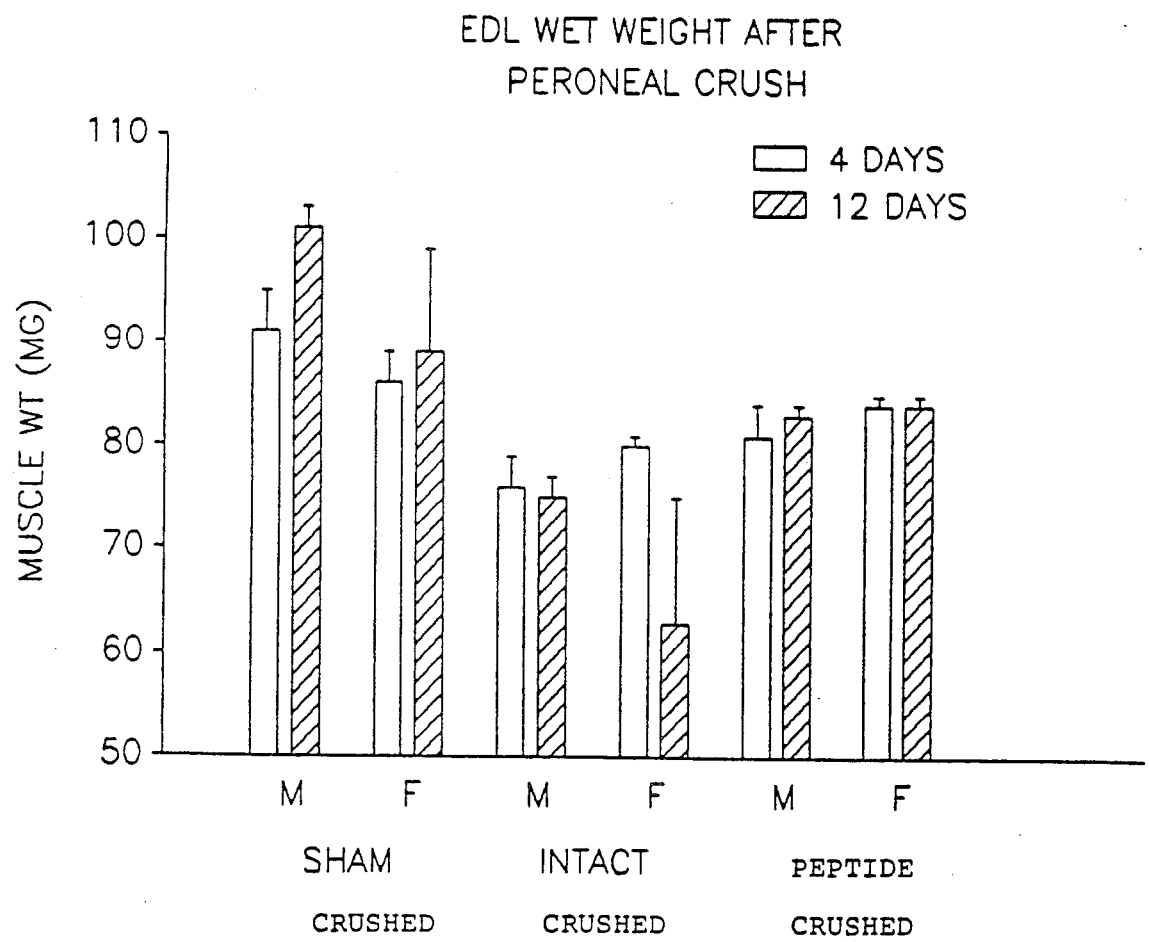
FIG. 1 is a graph showing the effect of BIM-21009 in promoting regrowth of denervated muscle, as determined by wet muscle weights.

We now describe preferred embodiments of the invention.

LHRH antagonsts useful for treating injured nerve tissue may be found in the publications cited above in the Background section, and in the following, each of which is hereby incorporated by reference: Coy et al. U.S. Pat. No. 4,632,979; Coy et al., U.S. Ser. No. 352,140, filed May 15, 1989; Coy et al., U.S. Ser. No. 065,756, filed June 23, 1987; Coy et al., U.S. Ser. No. 879,338, filed June 27, 1986; Coy et al., EP0 225 746; Folkers et al., U.S. Pat. No. 4,642,332; Folkers et al., 1984, Biochem. Biophys. Research Comm. 123:1221; Folkers et al., 1984, Z. Naturforsch.B, 39:528; Folkers et al., 1985, Z. Naturforsch.B, 40:313; Nestor et al., 1984, J. Med. Chem. 27:1170); Nestor et al., EP0 277 829; Nestor et al., EP0 049 628; Nestor et al., EP0 097 031; Nestor et al., 1984, J. Med. Chem. 27:1170; Kent et al., EP0 052 510; Coy et al., U.S. Pat. No. 4,431,635; Coy et al., U.S. Pat. No. 4,317,315; Coy et al., EP0 081 877; Coy et al., 1982, Endocrinology 110:1445; Rivier et al., U.S. Pat. No. 4,444,759; Rivier et al., EP0 038 135; Bauer et al., U.S. Pat. No. 4,395,403; Vale et al., GB 2009182, filed Nov. 30, 1978; Beddell et al., U.S. Pat. No. 4,075,191.

These LHRH analogs can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

A therapeutically effective amount of the LHRH antagonist can be administered in combination with a pharmaceutically acceptable carrier substance, e.g., magnesium carbonate or lactose. This composition can be in the form of a pill, tablet, capsule, liquid, or sustained release tablet for oral administration; a liquid spray for nasal administration; or a liquid for intravenous, subcutaneous, parenteral, or intraperitoneal administration.

Another preferred form for administration is an injectible suspension of the peptide analog with a bioerodible, biocompatible polymer matrix capable of effecting sustained release of the analog. Other suitable forms are analog/polymer implants, transdermal patches, transmucosal patches and compositions usable with iontophoretic techniques.

Testing

LHRH analogs can be tested for effectiveness in treating injured nerve tissue or preserving muscle mass according to the testing procedures described below for the LHRH analog BIM-21009. BIM-21009 is an antagonist of LHRH activity having the amino acid formula N-Acetyl-D-Naphthylalanine-D-para-Cl-Phe-D-Phe-Ser-Tyr-D-Arg-Phe-Arg-Pro-D-Ala-$NH_2$. BIM-21009 was administered to animals both prior to and after denervation. The animals were prepared for treatment as follows.

Adult male and female Sprague Dawley rats (Hilltop) weighing approximately 250–275 g were housed in groups of three of the same sex and provided with Purina rat chow and water ad libitum. They were maintained in a 12L:12D photoperiod with lights off at 19:00 hr. Animals were divided into 2 groups having six subdivisions each of 5–7 animals: (1) four days post-lesion: "sham crushed" (i.e., sham nerve crush) males and females, "intact crushed" (i.e., nerve crush control group) males and females, and "LHRH antagonist treated and crushed" (i.e., peptide treatment after nerve crush, also referred to as "peptide crushed") males and females; and (2) twelve days post-lesion: sham crushed males and females, intact crushed males and females, and LHRH treated and crushed males and females.

All animals were anesthetized with an 8% solution of chloral hydrate (0.4 g/kg). An incision was made on the left leg and the peroneal nerve was exposed at its site of entrance into the peroneal longus muscle. The nerve was crushed with a watchmaker forcep having a uniformly filed tip of 0.2 mm, by applying pressure on the nerve for 10 seconds, rotating the forceps, and applying pressure again on the opposite side for another 10 seconds. After crush, this area of approximately 1 mm becomes translucid. This modified crush method gives well-defined axonal interruption without disrupting the connective tissue sheaths or blood vessels in the region.

All chemically treated animals received 1 s.c. injection of the LHRH antagonist BIM-21009 at a dosage of 5 mg/kg 24 hrs prior to denervation. Animals in the 12 day groups received an additional injection of 5 mg/kg 6 days after the first injection.

Dissections were performed between 13:00 and 15:00 hrs. The peroneal nerve was allowed to regenerate for 4 or 12 days, after which the animals were anesthetized with chloral hydrate (0.4 g/kg), the extensor digitorum longus ("EDL") was dissected, frozen on powdered dry ice and stored at −70° C. until the day of the assay.

Blood samples were drawn from the inferior vena cava using a 10 ml syringe which contained 0.7 g of EDTA as an anticoagulant. The blood was kept on ice, centrifuged in a refrigerated centrifuge at 1700 g for 25 min., and stored at −70° C. until the day of radioimmunoassay.

Testosterone levels were determined using the Coat-A-Count Free Testosterone RIA (Diagnostic Products Corporation) with a sensitivity of up to 0.15 pg/ml. Estradiol levels were determined using the Coat-A-Count Free Estradiol RIA kit (Diagnostic Products Corp.)

Acetycholine Receptor Assay

The acetylcholine receptor assay was performed using a modified version of a method previously described by Bleisch et al. (1982, Ph.D. Thesis, New York University, New York.)). The EDL muscles were thawed, weighed, minced with a razor blade on ice and homogenized in a fresh solution of 1.5% Triton X-100 and 0.02% sodium azide in 50 mM $NaPO_4$ buffer (pH 7.2). 1/1000 aprotinin and 1/1000 of a saturated phenylmethylsulfonylfluoride (PMSF) solution in dimethylsulfoxide (DMSO) were added to inhibit proteases. The muscle extract was incubated for 1 hr. in a $H_2O$ bath at 30° C. with shaking every 15 min., centrifuged at 4° C. at 45K for 1 hr., the supernatant removed, frozen in a slush of ethanol and dry ice and stored at −70° C. until the day of the assay.

Torpedo acetylcholine receptors were used as controls. $^{125}I$ alpha bungarotoxin was purchased from New England Nuclear (NEX 126) with a specific activity of 16.6 uCi/ug when purchased. The toxin was purified by ion exchange chromatography using CM-52 cellulose resin (Sigma); the monoiodinated fraction was collected and stored at 4° C.

Acetylcholine receptor (ACh receptor or AChR) was measured as the number of AChR per muscle (pM/ug muscle or fM/ug protein) as determined by $^{125}I$-$\alpha$ bungarotoxin binding to AChR, muscle weight (wet); ug protein content per mg muscle weight. Detergent-extractable acetylcholine receptors (AChR) were measured as binding of $^{125}I$ $\alpha$-bungarotoxin. Briefly, 50 ul of extract muscle was incubated with 100 ul of 0.1% bovine serum albumin (BSA) in 10 mM $NaPO_4$ buffer (pH 7.2) at room temperature for 45 min. The samples were then incubated with 100 ul of $^{125}I$ $\alpha$-bungarotoxin for 3 hrs. at 30° C. and added to prefilled Bio Rex-70 $Na^+$ previously flushed with 3 ml of 0.01% Triton X-100 in 1 mM $NaPO_4$ and 1 ml of 1% BSA in 1 mM $NaPO_4$ (pH 7.2). The samples were allowed to flow into the column and were eluted with 3 ml of 0.01% Triton X-100 in 1 mM $NaPO_4$ (pH 7.2). The eluate was collected in polypropylene tubes and each sample was counted in a gamma scintillation counter for 1 min.

The Lowry Method was used for protein determinations. Statistical analysis was performed using $2 \times 2$ ANOVA, 1 way ANOVA. Tukey's HSD test was used for post-hoc comparisons.

Results

Figure 2:
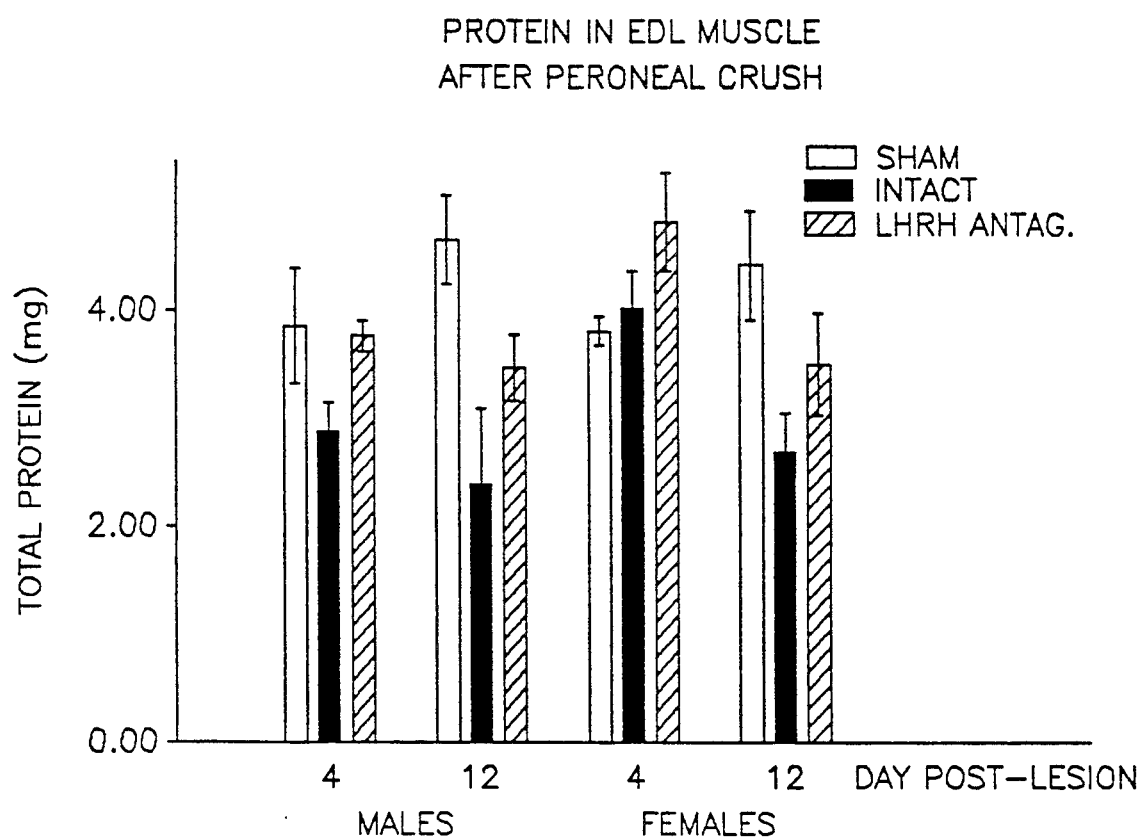
FIG. 2 is a graph showing the effect of BIM-21009 in promoting regrowth of denervated muscle, as determined by total protein weights.

Experimental results are presented in Table 1 and FIGS. 1–5. Table 1 is a tabulation of data presented in FIGS. 1, 2, 3 and 5. The results presented in Table 1 and FIG. 1 show that, both at 4 days and at 12 days post-lesion, the atrophy of the denervated EDL muscle was significantly decreased in the group treated with BIM-21009 ("Peptide crushed") than in the crushed control group ("Intact crushed"). However, this effect was less striking in females than in males, since denervation atrophy in females is less than in males. Recovery from the crush-induced muscle atrophy was associated with an increase in protein content rather than fat accumulation or edema (FIG. 2). This was evident in females as well as males.

Figure 3:
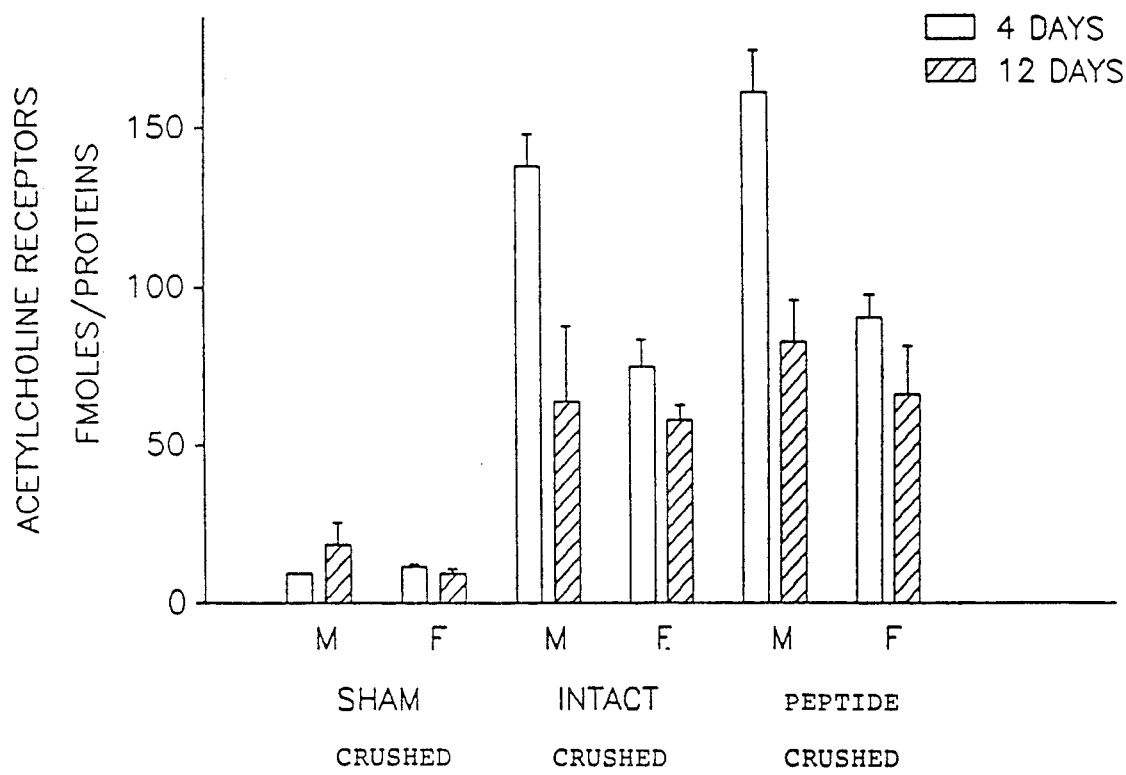
FIG. 3 is a graph showing the effect of BIM-21009 in promoting proliferation of acetylcholine receptors in denervated muscle, as determined by the numbers of the receptors (fmoles) per μg protein.
Figure 4:
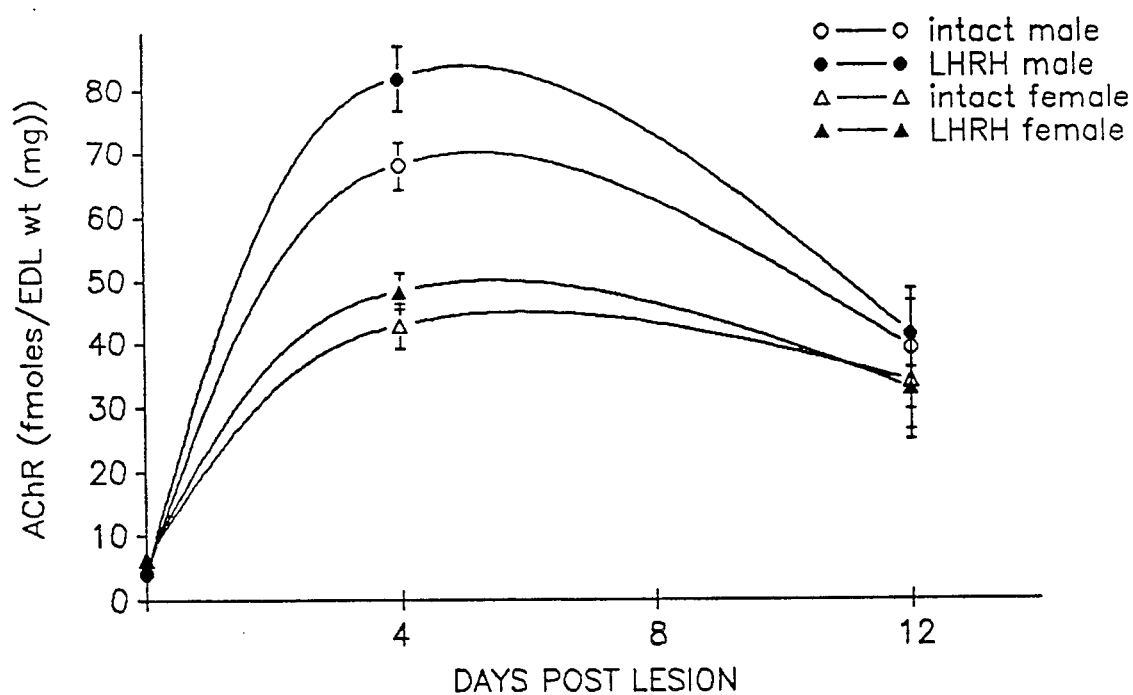
FIG. 4 is a graph showing the effect of BIM-21009 in promoting proliferation of acetylcholine receptors in denervated muscle as a function of time, as determined by the numbers of the receptors (fmoles) per mg muscle.
Figure 5:
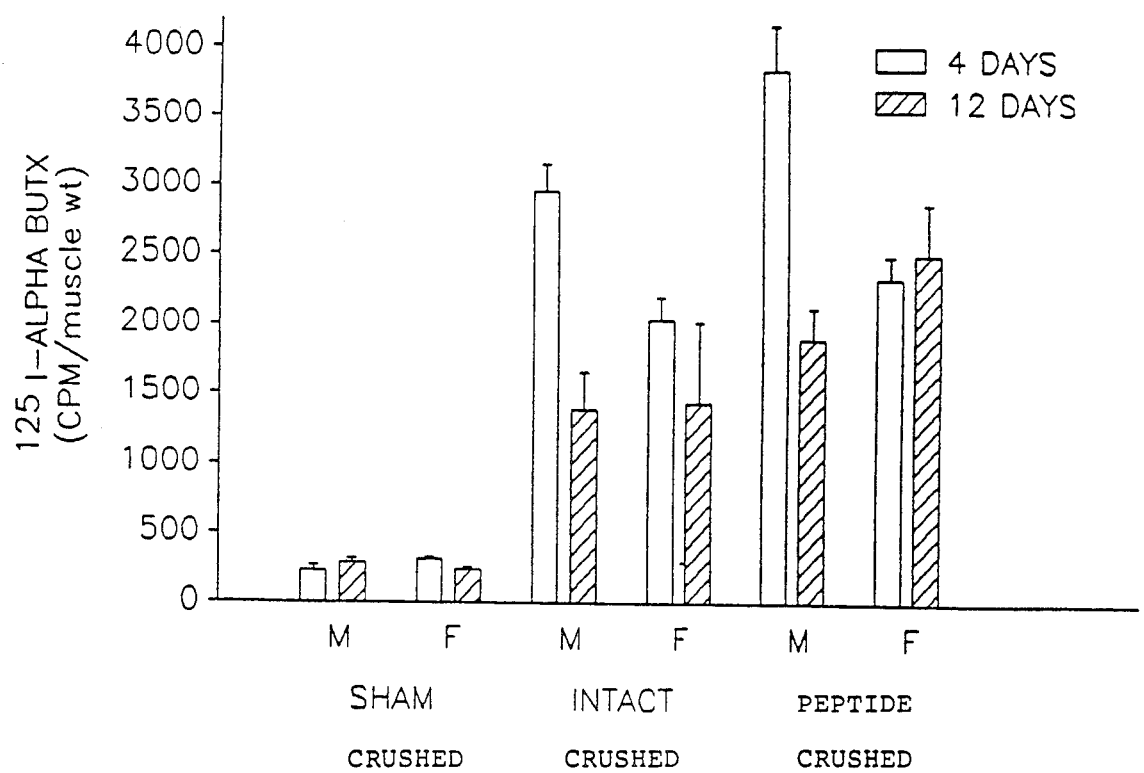
FIG. 5 is a graph showing the effect of BIM-21009 in promoting proliferation of acetylcholine receptors in denervated muscle, as determined by binding of $^{125}$I-bungarotoxin to the receptor (cpm) per mg muscle.

Results presented in FIGS. 3, 4, and 5 show that AChR numbers in sham crushed males were not significantly different from sham crushed females. Results presented in FIGS. 3 and 4 show that, at 4 days post-lesion, untreated crushed male rats with intact gonads had significantly more AChR (fM/mg of muscle or fM/ug protein) than untreated crushed females with intact gonads.

Results presented in FIG. 4 show that treatment with BIM-21009 significantly changes the AChR number/muscle weight ratio for males with intact gonads, in that this ratio was higher than in the crushed untreated controls with intact gonads. In addition, these results and those presented in FIGS. 3 and 5 show that crushed untreated males had a significantly higher ratio of AChR/mg muscle than sham operated untreated males. Results presented in FIGS. 3 and 4 demonstrate that male and female rats treated with BIM-21009 have significantly higher ratio of AChR number/muscle (fM AChR/mg muscle or fM/ug protein) than do the crushed group with intact gonads; at 4 days post-lesion, males in both the intact crushed and peptide crushed groups have significantly more receptors than females. Results presented in FIG. 5 also show that treatment with BIM-21009 gave a higher ratio of cpm/mg muscle than for the intact crushed groups. This result was consistent for both males and females.

The results demonstrate that, while there is no difference in the number of ACh receptors in the EDL muscle of normal adult males and females, there are sex differences in ACh receptor number during early reinnervation of the denervated EDL muscle, with males having more ACh receptors than the females. Treatment with BIM-21009 results in a dramatic increase in the number of ACh receptors in both sexes, at 4 days after nerve crush, but it is more marked in males. These results also show that the duration of effect is limited to early treatment. Treatment with BIM-21009 shows a maximal effect at day 4 post-lesion and a minimal or null effect by day 12.

Treatment with BIM-21009 also protects the EDL muscle in the males from denervation atrophy. At 12 days after denervation, at which time functional recovery has occurred, there are once again no sex differences in ACh receptor number. It appears that treatment with BIM-21009 has a marked effect on receptor number during the period of plasticity engendered by the processes of regeneration.

Any LHRH antagonist can be screened for nerve regrowth activity using the above described assay systems.

Use

Administration of an LHRH analog according to the method of the invention may be, e.g., orally, intravenously, parenterally, nasally, or by suppository. Administration of the analog directly after injury is most effective for treatment of injured or traumatized nerve tissue.

The analogs can be administered to a patient in a dosage of 10 mcg/kg/day to 1000 mcg/kg/day, preferably 25-250 mcg/kg/day.

Other embodiments are within the following claims.

TABLE 1

| | Muscle wt (mg) | Proteins (ug) | AChR (cpm) | AChR (fmol) |
|---|---|---|---|---|
| 4 DAY | | | | |
| Sham Crushed | | | | |
| Males (4) | 91.3 ±3.7 | 4.29 ±0.35 | 2.33 ±0.37 | 8.93 ±0.90 |
| Females (6) | 86.4 ±3.1 | 4.86 ±0.25 | 3.08 ±0.19 | 11.14 ±0.87 |
| Intact crushed | | | | |
| Males (7) | 75.8 ±2.8 | 3.82 ±0.26 | 29.63 ±1.92 | 135.85* ±9.60 |
| Females (7) | 83.1 ±1.1 | 5.06 ±0.48 | 20.41 ±1.62 | 74.48 ±9.06 |
| Peptide crushed | | | | |
| Males (6) | 81.2 ±3.3 | 4.05 ±0.36 | 38.37 ±3.26 | 166.96* ±13.50 |
| Females (6) | 83.8 ±1.3 | 4.58 ±0.25 | 23.39 ±1.62 | 90.07 ±8.46 |
| 12 DAY | | | | |
| Sham crushed | | | | |
| Males (5) | 100.6 ±2.4 | 5.03 ±0.44 | 2.89 ±0.27 | 18.02 ±7.80 |
| Females (3) | 89.3 ±10.0 | 5.03 ±1.12 | 2.38 −0.19 | 9.08 ±1.59 |
| Intact crushed | | | | |
| Males (2) | 63.4 ±12.0 | 4.38 ±1.47 | 14.36 ±0.58 | 57.82 ±6.82 |
| Females (4) | 75.2 ±2.4 | 4.92 ±0.91 | 13.90 ±0.27 | 63.62 ±27.44 |
| Peptide crushed | | | | |
| Males (4) | 83.1 ±1.1 | 4.34 ±0.40 | 19.01 ±2.29 | 82.09 ±15.87 |
| Females (5) | 84.0 ±1.1 | 4.23 ±0.23 | 15.34 ±3.67 | 65.74 ±16.78 |

We claim:

1. A method for promoting the expression of acetylcholine receptors in a mammal, said method comprising administering to said mammal effective amount of N-Acetyl-D-Naphthylalanine-D-para-Cl-Phe-D-Phe-Ser-Tyr-D-Arg-Phe-Arg-Pro-D-Ala-NH$_2$.

2. A method for inhibiting muscle wasting in a mammal, said method comprising administering to said mammal a muscle preserving effective amount of N-Acetyl-D-Naphthylalanine-D-para-Cl-Phe-D-Phe-Ser-Tyr-D-Arg-Phe-Arg-Pro-D-Ala-NH$_2$.

* * * * *